United States Patent
Houser

(10) Patent No.: US 12,251,124 B2
(45) Date of Patent: *Mar. 18, 2025

(54) SURGICAL INSTRUMENT WITH STAGED APPLICATION OF ELECTROSURGICAL AND ULTRASONIC ENERGY

(71) Applicant: Cilag GmbH International, Zug (CH)

(72) Inventor: Kevin L. Houser, Springboro, OH (US)

(73) Assignee: Cilag GmbH International, Zug (CH)

( * ) Notice: Subject to any disclaimer, the term of this patent is extended or adjusted under 35 U.S.C. 154(b) by 638 days.

This patent is subject to a terminal disclaimer.

(21) Appl. No.: 17/508,073

(22) Filed: Oct. 22, 2021

(65) Prior Publication Data

US 2022/0104846 A1 Apr. 7, 2022

Related U.S. Application Data

(63) Continuation of application No. 16/549,834, filed on Aug. 23, 2019, now Pat. No. 11,246,622, which is a
(Continued)

(51) Int. Cl.
*A61B 17/32* (2006.01)
*A61B 18/14* (2006.01)
(Continued)

(52) U.S. Cl.
CPC .. *A61B 17/320092* (2013.01); *A61B 18/1445* (2013.01); *A61B 18/1447* (2013.01);
(Continued)

(58) Field of Classification Search
CPC ............... A61B 18/00; A61B 18/1447; A61B 2018/0063; A61B 2018/00654;
(Continued)

(56) References Cited

U.S. PATENT DOCUMENTS

| 5,322,055 A | 6/1994 | Davison et al. |
| 5,324,299 A | 6/1994 | Davison et al. |

(Continued)

FOREIGN PATENT DOCUMENTS

| CN | 1913840 A | 2/2007 |
| CN | 103635157 A | 3/2014 |

(Continued)

OTHER PUBLICATIONS

Chinese Office Action and Search Report Mar. 7, 2020, for Application No. 201680076966.0, 11 pages.
(Continued)

*Primary Examiner* — Tigist S Demie
(74) *Attorney, Agent, or Firm* — Frost Brown Todd LLP

(57) ABSTRACT

An apparatus includes a body, a shaft assembly, an end effector, and a control module. The shaft assembly extends distally from the body and includes an acoustic waveguide. The waveguide is configured to acoustically couple with an ultrasonic transducer. The end effector includes an ultrasonic blade, a clamp arm, an electrode, and a sensor. The ultrasonic blade is in acoustic communication with the waveguide. The clamp arm is operable to compress tissue against the ultrasonic blade. The electrode is operable to apply radiofrequency (RF) electrosurgical energy to tissue. The sensor is operable to sense a condition of tissue contacted by the end effector. The control module is operable to control delivery of ultrasonic power and RF electrosurgical energy through the end effector based on data from the sensor.

20 Claims, 8 Drawing Sheets

Related U.S. Application Data continuation of application No. 14/983,634, filed on Dec. 30, 2015, now Pat. No. 10,470,791.

(51) Int. Cl.
  *A61B 17/00* (2006.01)
  *A61B 17/29* (2006.01)
  *A61B 18/00* (2006.01)
  *A61B 18/12* (2006.01)

(52) U.S. Cl.
  CPC ............... *A61B 2017/00389* (2013.01); *A61B 2017/2946* (2013.01); *A61B 2017/320094* (2017.08); *A61B 2017/320095* (2017.08); *A61B 2018/00202* (2013.01); *A61B 2018/00404* (2013.01); *A61B 2018/00595* (2013.01); *A61B 2018/00601* (2013.01); *A61B 2018/00607* (2013.01); *A61B 2018/00619* (2013.01); *A61B 2018/0063* (2013.01); *A61B 2018/00642* (2013.01); *A61B 2018/00654* (2013.01); *A61B 2018/00666* (2013.01); *A61B 2018/00708* (2013.01); *A61B 2018/00815* (2013.01); *A61B 2018/00875* (2013.01); *A61B 2018/00922* (2013.01); *A61B 2018/00994* (2013.01); *A61B 2018/126* (2013.01); *A61B 2018/1455* (2013.01); *A61B 18/1492* (2013.01)

(58) Field of Classification Search
  CPC ........... A61B 2018/00708; A61B 2018/00815; A61B 2018/00875; A61B 2018/00994; A61B 2018/126; A61B 2018/1455
  See application file for complete search history.

(56) References Cited

U.S. PATENT DOCUMENTS

| | | |
|---|---|---|
| 5,873,873 A | 2/1999 | Smith et al. |
| 5,980,510 A | 11/1999 | Tsonton et al. |
| 6,283,981 B1 | 9/2001 | Beaupre |
| 6,309,400 B2 | 10/2001 | Beaupre |
| 6,325,811 B1 | 12/2001 | Messerly |
| 6,423,082 B1 | 7/2002 | Houser et al. |
| 6,500,176 B1 | 12/2002 | Truckai et al. |
| 6,773,444 B2 | 8/2004 | Messerly |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,544,200 B2 | 6/2009 | Houser et al. |
| 8,057,498 B2 | 11/2011 | Robertson |
| 8,058,771 B2 | 11/2011 | Giordano et al. |
| 8,461,744 B2 | 6/2013 | Wiener et al. |
| 8,591,536 B2 | 11/2013 | Robertson |
| 8,623,027 B2 | 1/2014 | Price et al. |
| 8,663,220 B2 | 3/2014 | Weiner et al. |
| 8,911,460 B2 | 12/2014 | Neurohr et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 10,433,863 B2 | 10/2019 | Glutz et al. |
| 10,470,791 B2 | 11/2019 | Houser |
| 11,246,622 B2 | 2/2022 | Houser |
| 2006/0079874 A1 | 4/2006 | Faller et al. |
| 2007/0011713 A1 | 1/2007 | Abramson et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2009/0030477 A1 | 1/2009 | Jarrard |
| 2012/0112687 A1 | 5/2012 | Houser et al. |
| 2012/0116265 A1 | 5/2012 | Houser et al. |
| 2012/0116364 A1* | 5/2012 | Houser ................. A61B 46/10 606/1 |
| 2012/0116391 A1* | 5/2012 | Houser ................. A61B 34/76 606/1 |
| 2014/0005701 A1 | 1/2014 | Olson et al. |
| 2014/0371735 A1 | 12/2014 | Long |
| 2015/0080924 A1 | 3/2015 | Stulen et al. |
| 2015/0141981 A1* | 5/2015 | Price ................. A61B 18/1445 606/38 |
| 2015/0148834 A1 | 5/2015 | Gee et al. |
| 2015/0245850 A1 | 9/2015 | Hibner et al. |

FOREIGN PATENT DOCUMENTS

| | | |
|---|---|---|
| EP | 1810628 B1 | 7/2009 |
| JP | 2007-229454 A | 9/2007 |
| JP | 2009-247887 A | 10/2009 |
| JP | 2015-521899 A | 8/2015 |

OTHER PUBLICATIONS

Chinese Office Action dated Jan. 29, 2021, for Application No. 201680076966.0, 10 pages.

Indian Office Action dated Aug. 19, 2021, for Application No. 201817022180, 5 pages.

International Search Report and Written Opinion dated Mar. 20, 2017, for International Application No. PCT/US2016/066472, 12 pages.

Japanese Office Action and First Search Report dated Nov. 24, 2020, for Application No. 2018-534720, 19 pages.

U.S. Appl. No. 61/410,603, entitled "Energy-Based Surgical Instruments," filed Nov. 5, 2010.

U.S. Appl. No. 62/265,611, entitled "End Effector for Instrument with Ultrasonic and Electrosurgical Features," filed Dec. 11, 2015.

* cited by examiner

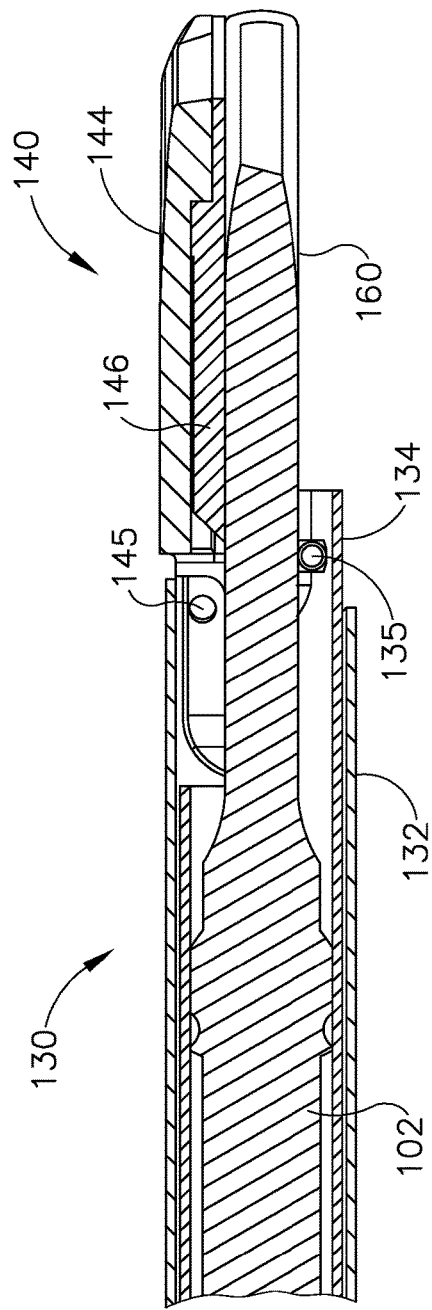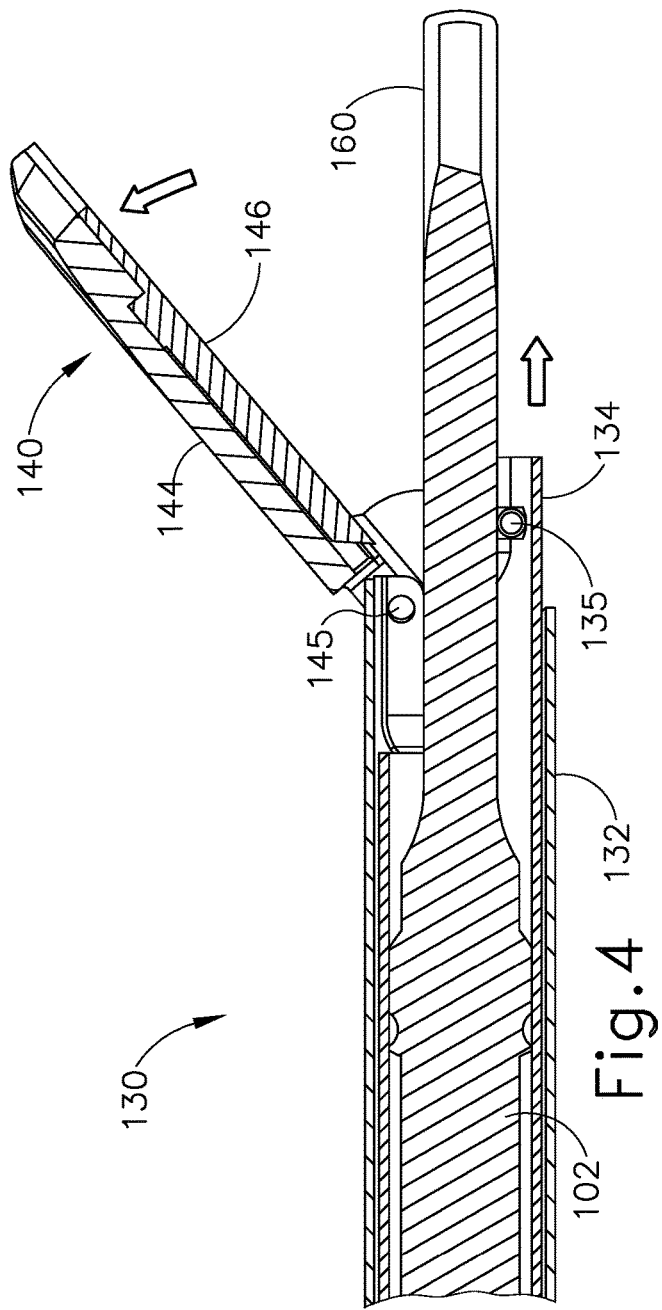

SURGICAL INSTRUMENT WITH STAGED APPLICATION OF ELECTROSURGICAL AND ULTRASONIC ENERGY

This application is a continuation of U.S. patent application Ser. No. 16/549,834, filed Aug. 23, 2019, entitled "Surgical Instrument with Staged Application of Electrosurgical and Ultrasonic Energy," published as U.S. Pat. Pub. No. 2020/0046402 on Feb. 13, 2020, issued as U.S. Pat. No. 11,246,622 on Feb. 15, 2022, which is a continuation of U.S. patent application Ser. No. 14/983,634, filed Dec. 30, 2015, entitled "Surgical Instrument with Staged Application of Electrosurgical and Ultrasonic Energy," issued as U.S. Pat. No. 10,470,791 on Nov. 12, 2019.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drove the blade element may be varied (e.g., in real time) based on sensed parameters such as tissue impedance, tissue temperature, tissue thickness, and/or other factors. Some instruments have a clamp arm and clamp pad for grasping tissue with the blade element.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Clamp pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

Some instruments are operable to seal tissue by applying radiofrequency (RF) electrosurgical energy to the tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and radiofrequency (RF) electrosurgical energy to tissue. Examples of such instruments are described in U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pat. No. 8,663,220, entitled "Ultrasonic Electrosurgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3 depicts a cross-sectional side view of an end effector of the instrument of FIG. 2 in a closed position;

FIG. 4 depicts a cross-sectional side view of the end effector of FIG. 3 in an open position;

Figure 1:
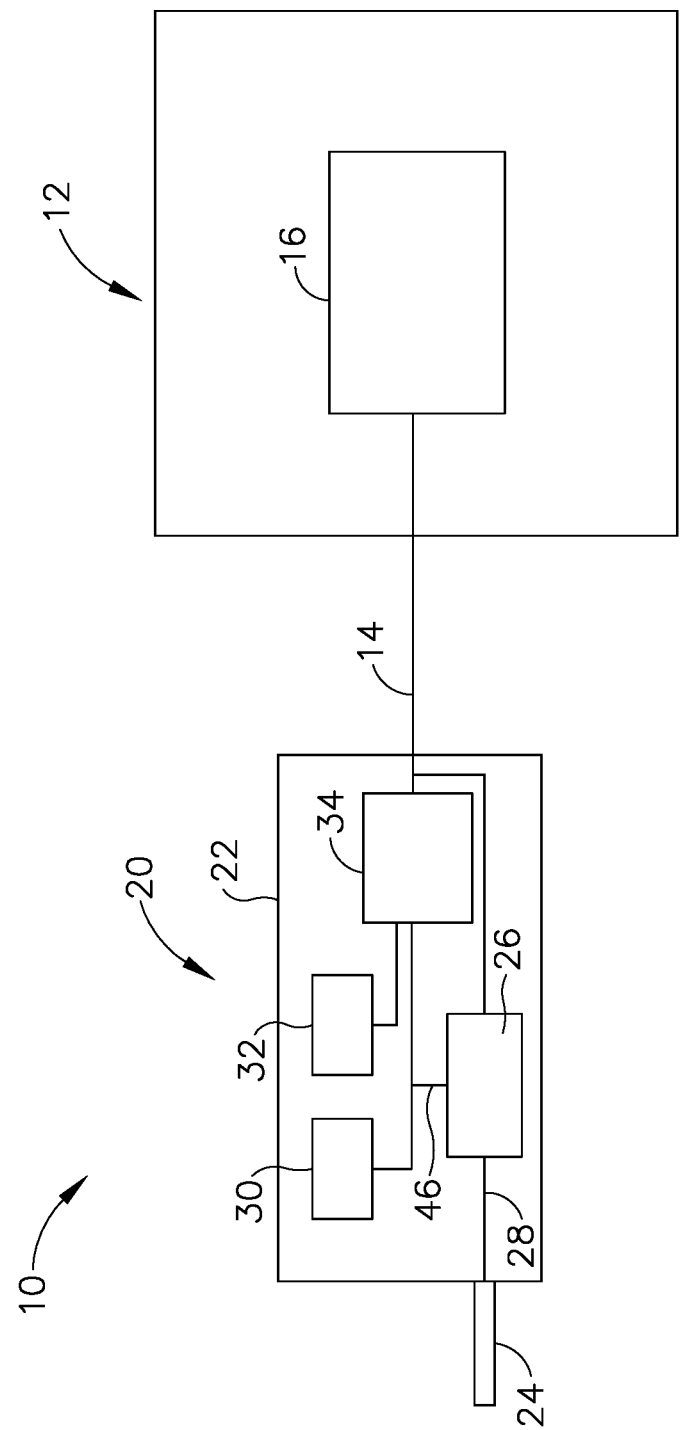
FIG. 1 depicts a block schematic view of an exemplary surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. OVERVIEW OF EXEMPLARY ULTRASONIC SURGICAL SYSTEM

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handle assembly (22), which is configured to be grasped in one hand (or two hands) of an operator and manipulated by one hand (or two hands) of the operator during a surgical procedure. For instance, in some versions, handle assembly (22) may be grasped like a pencil by the operator. In some other versions, handle assembly (22) may include a scissor grip that may be grasped like scissors by the operator. In some other versions, handle assembly (22) may include a pistol grip that may be grasped like a pistol by the operator. Of course, handle assembly (22) may be configured to be gripped in any other suitable fashion. Furthermore, some versions of instrument (20) may substitute handle assembly (22) with a body that is coupled to a robotic surgical system that is configured to operate instrument (20) (e.g., via remote control, etc.). In the present example, a blade (24) extends distally from the handle assembly (22). Handle assembly (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handle assembly (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (nλ/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handle assembly (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handle assembly (22). For instance, in some such versions, generator (12) only communicates one type of electrical power (e.g., just one voltage and/or current available) to handle assembly (22), and control circuitry (16) within handle assembly (22) is operable to modify the electrical power (e.g., the voltage of the electrical power), in accordance with selections made by the operator via control selector (30), before the electrical power reaches ultrasonic transducer (26). Furthermore, generator (12) may be incorporated into handle assembly (22) along with all other components of surgical system (10). For instance, one or more batteries (not shown) or other portable sources of power may be provided in handle assembly (22). Still other suitable ways in which the components depicted in FIG. 1 may be rearranged or otherwise configured or modified will be apparent to those of ordinary skill in the art in view of the teachings herein.

II. OVERVIEW OF EXEMPLARY ULTRASONIC SURGICAL INSTRUMENT

The following discussion relates to various exemplary components and configurations of instrument (20). It should be understood that the various examples of instrument (20) described below may be readily incorporated into surgical system (10) as described above. It should also be understood that the various components and operabilities of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
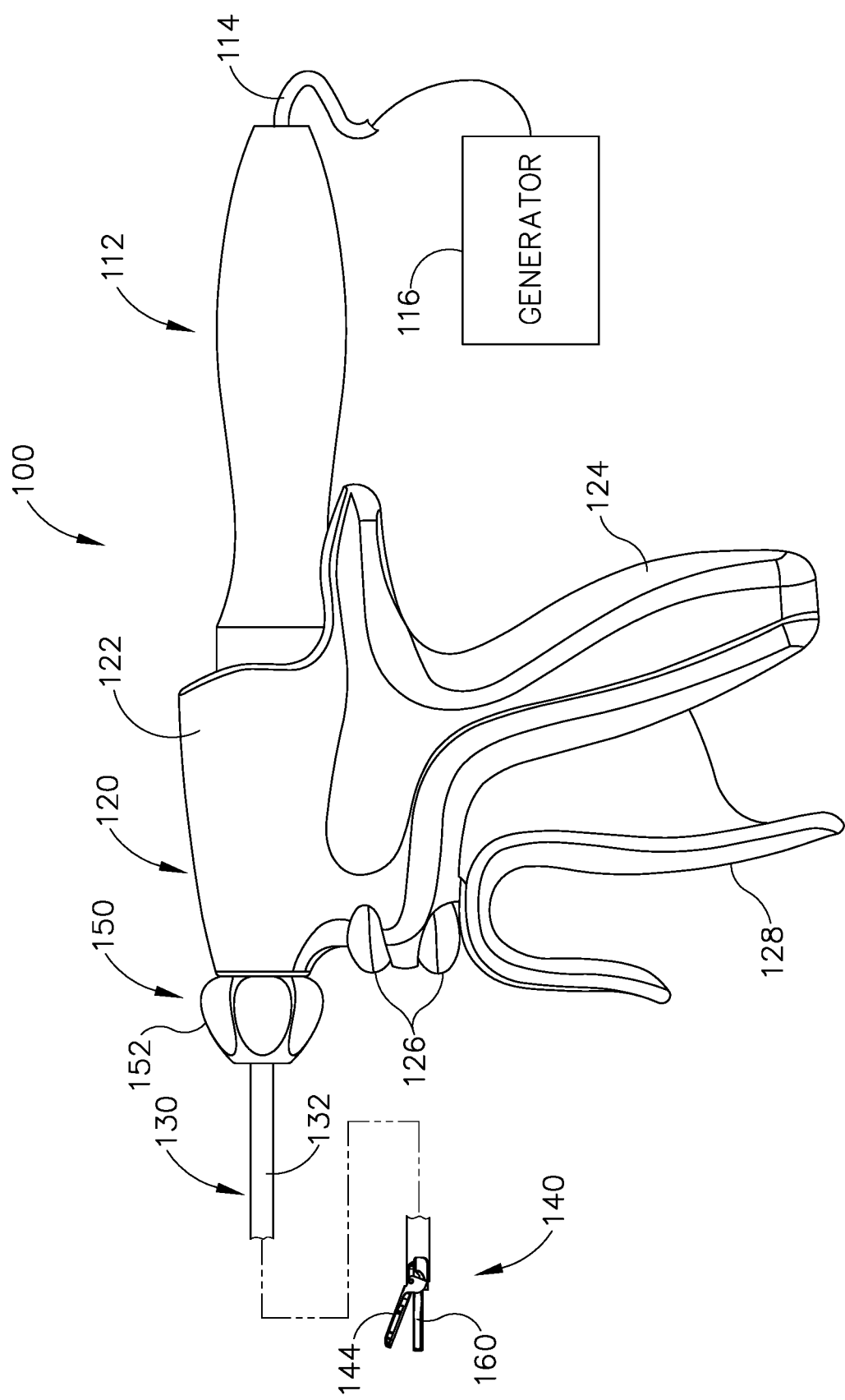
FIG. 2 depicts a side elevational view of an exemplary surgical instrument that may be incorporated into the system of FIG. 1.

FIGS. 2-4 illustrate an exemplary ultrasonic surgical instrument (100). At least part of instrument (100) may be constructed and operable in accordance with at least some of the teachings of U.S. Pat. Nos. 5,322,055; 5,873,873; 5,980,510; 6,325,811; 6,773,444; 6,783,524; 8,461,744; 8,623,027; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028,717, issued as U.S. Pat. No. 10,172,636 on Jan. 8, 2019. The disclosures of each of the foregoing patents, publications, and applications are incorporated by reference herein. As described therein and as will be described in greater detail below, instrument (100) is operable to cut tissue and seal or weld tissue (e.g., a blood vessel, etc.) substantially simultaneously. It should also be understood that instrument (100) may have various structural and functional similarities with the HARMONIC ACER Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (100) of the present example comprises a handle assembly (120), a shaft assembly (130), and an end effector (140). Handle assembly (120) comprises a body (122) including a pistol grip (124) and a pair of buttons (126). Handle assembly (120) also includes a trigger (128) that is pivotable toward and away from pistol grip (124). It should be understood, however, that various other suitable configurations may be used, including but not limited to a pencil-grip configuration or a scissor-grip configuration. End effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 4.

An ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN04, GEN11, or GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Blade (160) of the present example is operable to vibrate at ultrasonic frequencies in order to effectively cut through and seal tissue, particularly when the tissue is being clamped between clamp arm (144) and blade (160). Blade (160) is positioned at the distal end of an acoustic drivetrain. This acoustic drivetrain includes transducer assembly (112) and an acoustic waveguide (102). Transducer assembly (112) includes a set of piezoelectric discs (not shown) located proximal to a horn (not shown) of rigid acoustic waveguide (102). The piezoelectric discs are operable to convert electrical power into ultrasonic vibrations, which are then transmitted along acoustic waveguide (102), which extends through shaft assembly (130), to blade (160) in accordance with known configurations and techniques. By way of example only, this portion of the acoustic drivetrain may be configured in accordance with various teachings of various references that are cited herein.

Waveguide (102) is secured within shaft assembly (130) via a pin (133), which passes through waveguide (102) and shaft assembly (130). Pin (133) is located at a position along the length of waveguide (102) corresponding to a node associated with resonant ultrasonic vibrations communicated through waveguide (102). When ultrasonic blade (160) is in an activated state (i.e., vibrating ultrasonically), ultrasonic blade (160) is operable to effectively cut through and seal tissue, particularly when the tissue is being clamped between clamp arm (144) and ultrasonic blade (160). It should be understood that waveguide (102) may be configured to amplify mechanical vibrations transmitted through waveguide (102). Furthermore, waveguide (102) may include features operable to control the gain of the longitudinal vibrations along waveguide (102) and/or features to tune waveguide (102) to the resonant frequency of the system.

In the present example, the distal end of blade (160) is located at a position corresponding to an anti-node associated with resonant ultrasonic vibrations communicated through waveguide (102), in order to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 50 kHz or 55.5 kHz. When transducer assembly (112) of the present example is activated, these mechanical oscillations are transmitted through waveguide (102) to reach blade (160), thereby providing oscillation of blade (160) at the resonant ultrasonic frequency. Thus, when tissue is secured between blade (160) and clamp arm (144), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. While some configurations for an acoustic transmission assembly and transducer assembly (112) have been described, still other suitable configurations for an acoustic transmission assembly and transducer assembly (112) will be apparent to one or ordinary skill in the art in view of the teachings herein. Similarly, other suitable configurations for end effector (140) will be apparent to those of ordinary skill in the art in view of the teachings herein.

An operator may activate buttons (126) to selectively activate transducer assembly (112) to activate blade (160). In the present example, two buttons (126) are provided—one for activating blade (160) at a low power and another for activating blade (160) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb about pistol grip (124), position their middle, ring, and/or little finger about trigger (128), and manipulate buttons (126) using their index finger. Of course, any other suitable techniques may be used to grip and operate instrument (100); and buttons (126) may be located at any other suitable positions.

Shaft assembly (130) of the present example comprises an outer sheath (132), an inner tube (134) slidably disposed within outer sheath (132), and a waveguide (102) disposed within inner tube (134). As will be discussed in more detail below inner tube (134) is operable to translate longitudinally within outer sheath (132) relative to outer sheath (132) to selectively pivot clamp arm (144) toward and away from blade (160). Shaft assembly (130) of the present example further includes a rotation assembly (150). Rotation assembly (150) is operable to rotate the entire shaft assembly (130) and end effector (140) relative to handle assembly (120) about a longitudinal axis of shaft assembly (130). In some versions, rotation assembly (150) is operable to selectively lock the angular position of shaft assembly (130) and end effector (140) relative to handle assembly (120) about the longitudinal axis of shaft assembly (130). For instance, a rotation knob (152) of rotation assembly (150) may be translatable between a first longitudinal position, in which shaft assembly (130) and end effector (140) are rotatable relative to handle assembly (120) about the longitudinal axis of shaft assembly (130); and a second longitudinal position, in which shaft assembly (130) and end effector (140) are not rotatable relative to handle assembly (120) about the longitudinal axis of shaft assembly (130). Of course, shaft assembly (130) may have a variety of other components, features, and operabilities, in addition to or in lieu of any of those noted above. Other suitable configurations for shaft assembly (130) will be apparent to those of ordinary skill in the art in view of the teachings herein.

As shown in FIGS. 3 and 4, end effector (140) includes ultrasonic blade (160) and clamp arm (144). Clamp arm (144) includes a clamp pad (146) secured to an underside of clamp arm (144), facing blade (160). By way of example only, clamp pad (146) may be formed of a polytetrafluoroethylene (PTFE) material and/or any other suitable material(s). By way of further example only, clamp pad (146) may be further constructed and operable in accordance with at least some of the teachings of U.S. Pat. No. 7,544,200, entitled "Combination Tissue Pad for Use with an Ultrasonic Surgical Instrument," issued Jun. 9, 2009, the disclosure of which is incorporated by reference herein.

Clamp arm (144) is pivotably coupled with a distal end of outer sheath (132) of shaft assembly (130) above ultrasonic blade (160) via a pin (145). As best seen in FIG. 4, a distal end of inner tube (134) is rotatably coupled with a proximal end of clamp arm (144) below ultrasonic blade (160) via a pin (135) such that longitudinal translation of inner tube (134) causes rotation of clamp arm (144) about pin (145) toward and away from ultrasonic blade (160) to thereby clamp tissue between clamp arm (144) and ultrasonic blade (160) to cut and/or seal the tissue. In particular, proximal longitudinal translation of inner tube (134) relative to outer sheath (132) and handle assembly (120) causes clamp arm (144) to move toward ultrasonic blade (160); and distal longitudinal translation of inner tube (134) relative to outer sheath (132) and handle assembly (120) causes clamp arm (144) to move away from ultrasonic blade (160).

In the present example, trigger (128) is pivotably coupled to handle assembly (120) and is further coupled with inner tube (134). In particular, pivoting of trigger (128) toward pistol grip (124) will cause proximal longitudinal translation of inner tube (134) relative to outer sheath (132) and handle assembly (120); and pivoting of trigger (128) away from pistol grip (124) will cause distal longitudinal translation of inner tube (134) relative to outer sheath (132) and handle assembly (120). Finally, because longitudinal translation of inner tube (134) causes rotation of clamp arm (144) toward and away from blade (160) as discussed above, it should be understood that pivoting of trigger (128) toward pistol grip (124) will cause clamp arm (144) to move toward ultrasonic blade (160); and that pivoting of trigger (128) away from pistol grip (124) will cause clamp arm (144) to move away from ultrasonic blade (160). Various suitable components and features that may be used to couple trigger (128) with inner tube (134) to provide this operation are disclosed in several of the references cited herein. Other suitable components and features that may be used to couple trigger (128) with inner tube (134) to provide this operation will be apparent to those of ordinary skill in the art in view of the teachings herein. It should also be understood that, in some variations, trigger (128) is operable to drive outer sheath (132) longitudinally while inner tube (134) remains stationary. In such versions, the translation of outer sheath (132) relative to inner tube (134) will similarly cause clamp arm (144) to pivot toward and away from ultrasonic blade (160).

Figure 5:
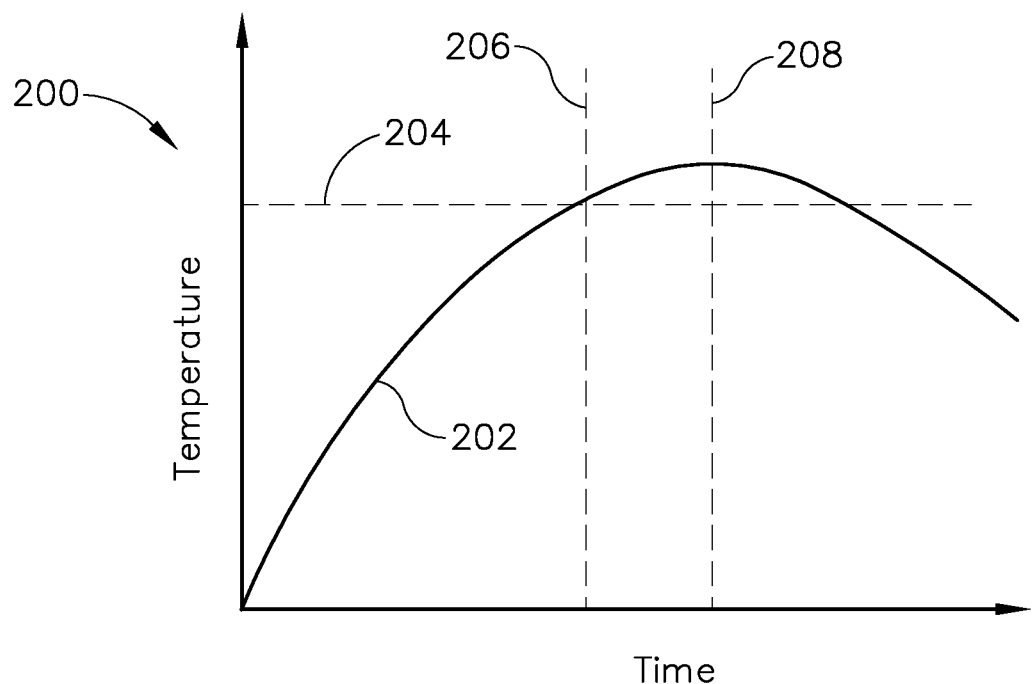
FIG. 5 depicts a graph showing a plot of tissue temperature versus time during activation of the end effector of FIG. 3.

FIG. 5 shows an exemplary graph (200) plotting tissue temperature (202) over the course of time while the tissue is clamped between clamp arm (144) and blade (160), with blade (160) being ultrasonically activated. The origin of this graph (200) represents the moment at which blade (160) is ultrasonically activated while the tissue is clamped between clamp arm (144) and blade (160). Line (204) represents the temperature level at which the tissue will begin to seal in response to the ultrasonic energy applied by blade (160). Similarly, line (206) represents the time at which the tissue begins to seal in response to the ultrasonic energy applied by blade (160). Line (208) represents the time at which the sealing of the tissue is complete. It should therefore be understood that the distance between lines (206, 208) represents a duration of time in which the tissue is being sealed by end effector (140).

It should also be understood that, in the present example, the temperature of the tissue continues to increase during the duration represented by the space between lines (206, 208). In some alternative versions, end effector (140) may include sensing capabilities such that end effector (140) is capable of maintaining the tissue temperature (202) substantially at the level associated with line (204) during the act of sealing (i.e., for the duration represented between line (206) and line (208)). In other words, the sensing capabilities may prevent the tissue from being overheated. Such sensing may be provided in accordance with the teachings of one or more references cited herein.

It should also be understood that, regardless of whether the temperature of the tissue continues to increase or stays generally flat for the duration represented between line (206) and line (208), such sensing may be used to automatically deactivate blade (160) once it is determined that the tissue has reached an appropriately sealed state (i.e., at the moment in time represented by line (208)). Again, such sensing and response may be provided in accordance with the teachings of one or more references cited herein.

In addition or in the alternative, the operator may rely on visual observation and/or tactile feedback through trigger (128) (e.g., feeling a difference in clamping force from clamp arm (144)) to determine when the tissue has reached an appropriately sealed state. The operator may then release the actuated button (126) to deactivate blade (160), and release trigger (128) to pivot clamp arm (144) away from the tissue, thereby manually establishing the end of the sealing stage represented by line (208).

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. No. 8,461,744 on June 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; and/or U.S. Pub. No. 2014/0114334, issued as U.S. Pat. No. 9,095,367 on Aug. 4, 2015. Additional merely illustrative variations for instrument (100) will be described in greater detail below. It should be understood that the below described variations may be readily applied to instrument (100) described above and any of the instruments referred to in any of the references that are cited herein, among others.

III. EXEMPLARY END EFFECTOR WITH COMBINED ULTRASONIC AND ELECTROSURGICAL CAPABILITIES

In some instances where a conventional form of instrument (20, 100) is used, it may take a relatively long time for the tissue to reach a temperature where the tissue begins to seal in response to activation of blade (160) while the tissue is being clamped between clamp arm (144) and blade (160). In other words, referring back to FIG. 5, the duration between the moment when blade (160) is activated and the moment represented by line (206) may be relatively long. It may therefore be desirable to speed up this "pre-heating" time. As described in greater detail below, one way in which this "pre-heating" time may be sped up is to apply RF electrosurgical energy to the tissue. As will also be described in greater detail below, this RF electrosurgical energy may be applied using the same end effector that applies ultrasonic energy to the tissue. In addition to providing a general combination of RF electrosurgical and ultrasonic capabilities, the below examples further provide control algorithms that regulate the application of these two different energy modalities to avoid overheating the tissue. The following examples thus provide enhanced pre-heating capabilities without resulting in overheating.

Figure 6:
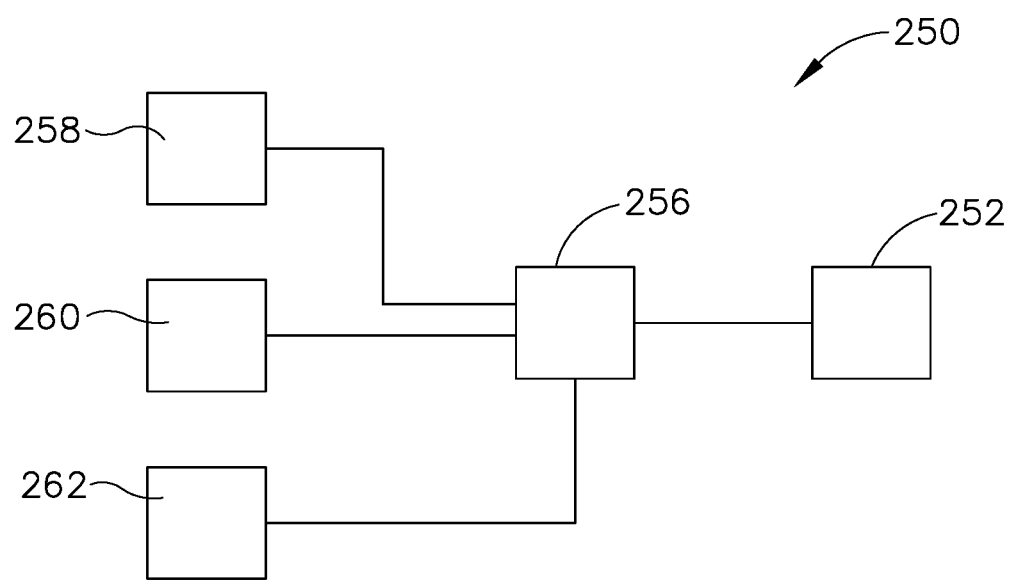
FIG. 6 depicts a schematic view of an exemplary arrangement of powered components that may be provided in a modified version of the instrument of FIG. 2.

FIG. 6 shows an arrangement of components that may be used to form a system (250) that is capable of providing enhanced tissue pre-heating capabilities without resulting in overheating of tissue. It should be understood that the components and operability of this system (250) may be readily combined with the components and operability of system (10) described above. System (250) of this example comprises a power source (252), a control module (256), an acoustic drivetrain (258), an RF electrosurgical drivetrain (260), and a sensor (262).

Power source (252) of the present example is operable to provide the electrical power to drive acoustic drivetrain (258) and RF electrosurgical drivetrain (260). Power source (252) is also operable to provide whatever electrical power is needed in order to render control module (256) operable. By way of example only, power source (252) may include a generator such as generator (12, 116) described above. As further described above, power source (252) may be integrated into a surgical instrument associated with system (250) or may be coupled with the surgical instrument via a cable such as cable (14, 114), etc. Various suitable forms that power source (252) may take will be apparent to those of ordinary skill in the art in view of the teachings herein.

Control module (256) of the present example may include a microprocessor and/or various other hardware components that are configured to execute a control logic. In particular, control module (256) is operable to selectively provide power from power source (252) to acoustic drivetrain (258) and RF electrosurgical drivetrain (260) in accordance with one or more control algorithms provided through control logic. In versions where sensor (262) is present, control module (256) receives data from sensor (262) and is thereby operable to factor in such data when executing the control logic. In some versions, control module (256) is integrated into power source (252) (e.g., in a generator (12, 116) that is separate from a surgical instrument associated with system (250)). In some other versions, control module (256) is integrated into a surgical instrument associated with system (250). Various suitable forms that control module (256) may take will be apparent to those of ordinary skill in the art in view of the teachings herein.

Acoustic drivetrain (258) of the present example is operable to generate and communicate ultrasonic vibrations in response to electrical power from power source (252), as regulated by control module (256). By way of example only, acoustic drivetrain (258) may comprise an ultrasonic transducer (26, 112), a waveguide (28), and an ultrasonic blade (24, 160) as described above. Other suitable forms that acoustic drivetrain (258) may take will be apparent to those of ordinary skill in the art in view of the teachings herein.

RF electrosurgical drivetrain (260) of the present example is operable to apply RF electrosurgical energy to tissue in response to electrical power from power source (252), as regulated by control module (256). By way of example only, RF electrosurgical drivetrain (260) may include a pair of electrodes and a corresponding pair of electrical conduits (e.g., wires, traces, etc.) that are coupled with control module (256). As described in greater detail below, the electrodes of RF electrosurgical drivetrain (260) may be integrated into the same end effector as the ultrasonic blade of acoustic drivetrain (258). For instance, a clamp arm such as clamp arm (144) may include two electrodes—each providing a different pole for the application of bipolar energy. As another merely illustrative example, a clamp arm such as clamp arm (144) may include a single electrode for providing one pole; while an ultrasonic blade such as blade (24, 160) may serve as another electrode to provide the other pole for application of bipolar energy. As yet another merely illustrative example, the end effector may include just one electrode (e.g., in a clamp arm such as clamp arm (144) or in an ultrasonic blade such as blade (24, 160)), and a conventional ground pad may be secured to the patient to provide another electrode such that the end effector is operable to apply monopolar energy to tissue. Other suitable forms that RF electrosurgical drivetrain (260) may take will be apparent to those of ordinary skill in the art in view of the teachings herein.

Sensor (262) of the present example is operable to sense a state of the tissue that is being engaged by the end effector of the instrument associated with system (250). In particular, sensor (262) is operable to sense one or more tissue conditions that would indicate that the tissue has reached the appropriate sealing temperature associated with line (204) as shown in FIG. 5 and as described above. By way of example only, sensor (262) may comprise a conventional temperature sensor. As another merely illustrative example, sensor (262) may comprise an impedance sensor (e.g., to the extent that the impedance of tissue is indicative of the tissue reaching an appropriate temperature or otherwise reaching a sealed state). As yet another merely illustrative example, sensor (262) may comprise a positive temperature coefficient (PTC) thermistor. Other suitable forms that sensor (262) may take will be apparent to those of ordinary skill in the art in view of the teachings herein. It should also be understood that sensor (262) may be incorporated into the end effector of the instrument associated with system (250) (e.g., in a clamp arm such as clamp arm (144)), such that the sensor (262) may directly contact the tissue that is being engaged by the end effector. In some versions of system (250), sensor (262) is omitted.

The following examples include various end effector configurations that may be incorporated into system (250) and various control algorithms that may be executed through system (250). In addition to having the features, configurations, and functionalities described below, the following examples may also have any of the various features, configurations, and/or functionalities taught in U.S. Pat. No. 8,663,220, entitled "Ultrasonic Electrosurgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and/or U.S. Patent App. No. 62/265,611, entitled "End Effector for Instrument with Ultrasonic and Electrosurgical Features," filed Dec. 11, 2015, disclosure of which is incorporated by reference herein. Various suitable ways in which the below teachings may be combined with teachings of those references (and/or combined with the teachings of the other references cited herein) will be apparent to those of ordinary skill in the art.

A Exemplary End Effector with Clamp Arm Having Electrode Pair

Figure 7:
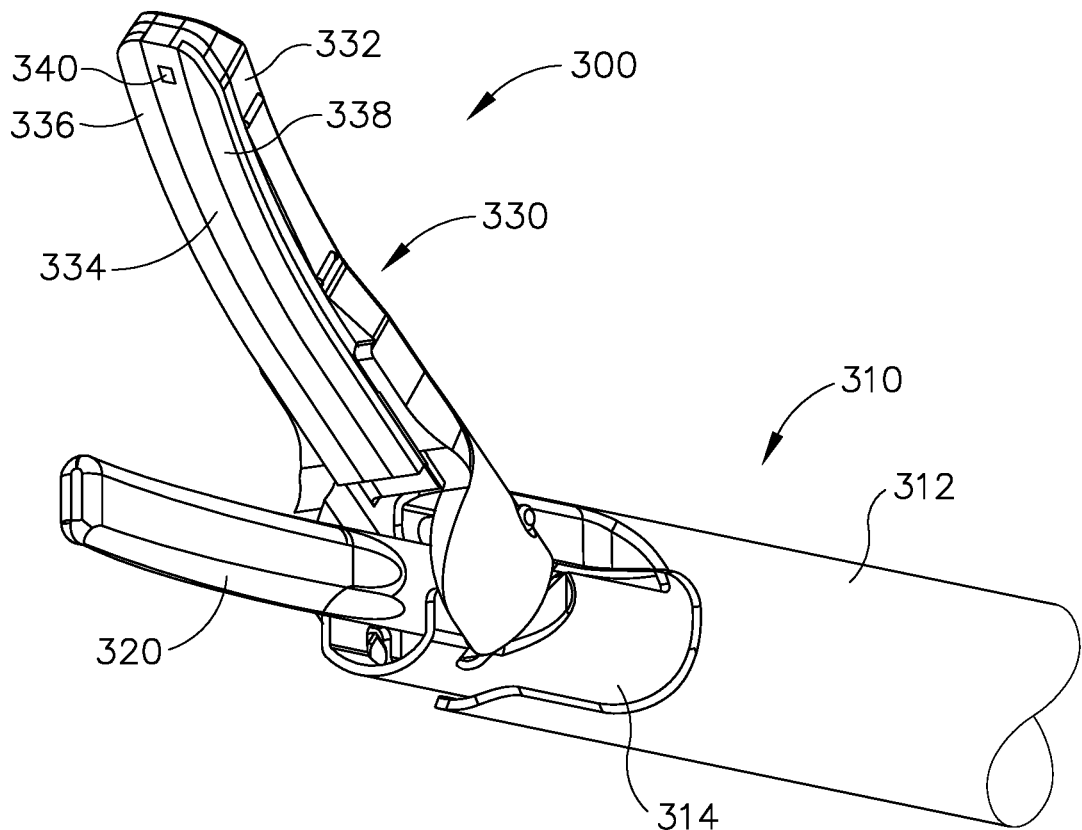
FIG. 7 depicts a perspective view of an exemplary alternative end effector that may be incorporated into the instrument of FIG. 2 to provide the arrangement of powered components of FIG. 6.
Figure 8:
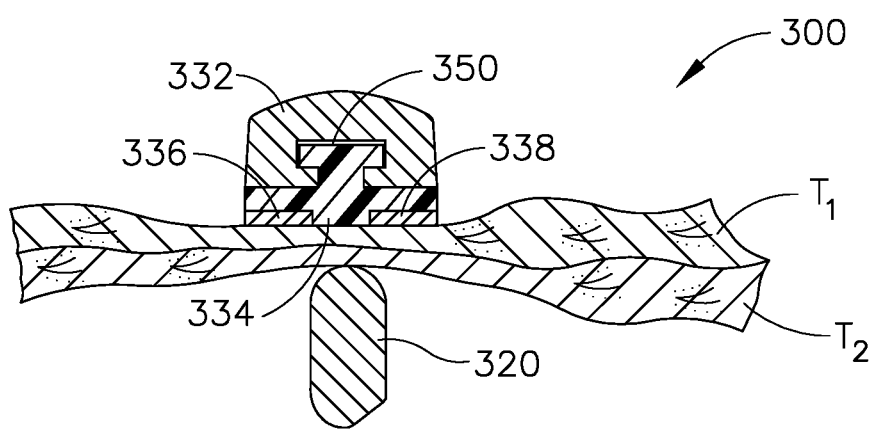
FIG. 8 depicts a cross-sectional end view of the end effector of FIG. 7 clamping tissue.

FIGS. 7-8 show an exemplary end effector (300) that may be incorporated into instrument (100) in place of end effector (140) in order to provide the functionality of system (250) described above. End effector (340) comprises a clamp arm (330) and an ultrasonic blade (320). End effector (340) is located at the distal end of a shaft assembly (310). Shaft assembly (310) includes an outer tube (312) and an inner tube (314). Clamp arm (330) is pivotably coupled with outer tube (312) and also with inner tube (314), such that clamp arm (330) is configured to pivot toward and away from blade (320) in response to relative movement between tubes (312, 314). Clamp arm (330) is thus pivotable just like clamp arm (144) described above. In some versions, outer tube (312) translates while inner tube (314) remains stationary in order to provide pivotal movement of clamp arm (330). In some other versions, inner tube (314) translates while outer tube (312) remains stationary in order to provide pivotal movement of clamp arm (330). It should also be understood that the connections between clamp arm (330) and tubes (312, 314) may be reversed such that the main pivot is on inner tube (314) instead of being on outer tube (312).

Blade (320) of the present example is configured and operable just like blade (24, 160) described above. Alternatively, blade (320) may have any other suitable configuration. It should be understood that, in the context of system (250) described above, blade (320) serves as part of acoustic drivetrain (258).

Clamp arm (330) of the present example is substantially similar to clamp arm (144) described above. In particular, clamp arm (330) comprises a clamp arm body (332) and a clamp pad (334) that is secured to clamp arm body (332) by a rail (350). By way of example only, clamp pad (334) may be formed of a polytetrafluoroethylene (PTFE) material and/or any other suitable material(s). Unlike clamp arm (144), clamp arm (330) of this example further includes a pair of electrodes (336, 338) and a sensor (340). In the present example, electrodes (336, 338) are configured to provide opposing poles for application of bipolar RF electrosurgical energy to tissue that contacts electrodes (336, 338). In some other versions, both electrodes (336, 338) provide one pole while blade (320) provides another pole for application of bipolar RF electrosurgical energy to tissue that contacts electrodes (336, 338) and blade (320). In either case, it should be understood that the material forming clamp pad (334) may have electrically insulative properties to prevent short circuiting between electrodes (336, 338). It should also be understood that, in the context of system described above, electrodes (336, 338) serve as part of RF electrosurgical drivetrain (260).

In the present example, electrodes (336, 338) extend along the full length of clamp pad (334) and are positioned at the laterally outermost regions of clamp pad (334). In some alternative versions, one or both of electrodes (336, 338) is/are positioned laterally inwardly from the positions shown in FIGS. 7-8, such that a portion of clamp pad (334) is positioned laterally outwardly from electrodes (336, 338). It should also be understood that three or more electrodes may be provided on clamp pad (334). In some versions, a center electrode extends longitudinally along at least part of the length of clamp pad (334), is laterally centered relative to clamp pad (334), and is recessed relative to the tissue contacting surfaces of clamp pad (334). Such positioning of an electrode may enable the electrode to contact tissue without being able to contact blade (320). Such recessing of an electrode may also be applied to more than one electrode in clamp pad (334), and is not necessarily limited to a single central electrode. Other suitable configurations and arrangements of electrodes (336, 338) will be apparent to those of ordinary skill in the art in view of the teachings herein.

Sensor (340) of the present example is located at the distal end of end effector (300) and is laterally positioned between electrodes (336, 338). This location is just one merely illustrative example. Other suitable locations for sensor (340) will be apparent to those of ordinary skill in the art in view of the teachings herein. It should also be understood that end effector (300) may include two or more sensors (340) if desired.

Sensor (340) of the present example is operable to sense a state of the tissue that is being engaged by clamp pad (334). In particular, sensor (340) is operable to sense one or more tissue conditions that would indicate that the tissue has reached the appropriate sealing temperature associated with line (204) as shown in FIG. 5 and as described above. By way of example only, sensor (340) may comprise a conventional temperature sensor. As another merely illustrative example, sensor (340) may comprise an impedance sensor (e.g., to the extent that the impedance of tissue is indicative of the tissue reaching an appropriate temperature or otherwise reaching a sealed state). As yet another merely illustrative example, sensor (340) may comprise a positive temperature coefficient (PTC) thermistor. As still another merely illustrative example, sensor (340) may comprise an optical sensor that is capable of determining the state of tissue based on optical sensing of the tissue. Other suitable forms that sensor (340) may take will be apparent to those of ordinary skill in the art in view of the teachings herein. It should be understood that, in the context of system (250) described above, sensor (340) serves the purpose of sensor (262).

As shown in FIG. 8, end effector (300) may be used to clamp tissue ($T_1$, $T_2$) between clamp arm (330) and blade (320). While end effector (300) is shown as clamping two layers of tissue ($T_1$, $T_2$), it should be understood that some uses of end effector (300) may include clamping only one layer of tissue ($T_1$, $T_2$). In either case, end effector (300) may be activated to either just seal the tissue ($T_1$, $T_2$) or cut and seal the tissue ($T_1$, $T_2$). When end effector (300) is activated to apply RF electrosurgical energy, the RF electrosurgical energy may flow through the tissue ($T_1$, $T_2$) that is positioned between electrodes (336, 338). In addition or in the alternative, when end effector (300) is activated to apply RF electrosurgical energy, the RF electrosurgical energy may flow through the tissue ($T_1$, $T_2$) that is positioned between electrodes (336, 338) and blade (320). When end effector (300) is activated to apply ultrasonic energy, blade (320) applies the ultrasonic energy to the region of tissue clamped between clamp arm (330) and blade (320). As described in greater detail below, end effector (300) may apply RF electrosurgical energy and ultrasonic energy separately in a sequence; or together simultaneously. In either case, control module (256) may determine the appropriate algorithm for applying RF electrosurgical energy and/or ultrasonic energy.

While end effector (300) applies RF electrosurgical energy and/or ultrasonic energy to the tissue ($T_1$, $T_2$), sensor (340) may continuously detect one or more conditions associated with the tissue ($T_1$, $T_2$) and provide data to control module (256). Control module (256) may process this data as a factor of a control algorithm that is used to determine whether and how to apply RF electrosurgical energy and/or ultrasonic energy to the tissue ($T_1$, $T_2$). Various examples of control algorithms are described in greater detail below, while other examples of control algorithms will be apparent to those of ordinary skill in the art in view of the teachings herein.

In some versions, electrodes (336, 338) comprise PTC material. In some such versions, electrodes (336, 338) provide a resistance value that increases as the temperature of the tissue ($T_1$, $T_2$) increases. In some such versions, as the resistance of electrodes (336, 338) increases in response to the temperature of the tissue ($T_1$, $T_2$) increasing, the RF electrosurgical energy provided by electrodes (336, 338) diminishes, perhaps even ceasing once the temperature of the tissue ($T_1$, $T_2$) exceeds a threshold. Thus, in a sense the PTC material of electrodes (336, 338) may serve as a sensor (340) in addition to serving as electrodes, since the PTC material is sensitive to the condition of the tissue ($T_1$, $T_2$) and effectively changes the delivery of RF electrosurgical energy to the tissue ($T_1$, $T_2$) based on the condition of the tissue ($T_1$, $T_2$). Of course, electrodes (336, 338) need not necessarily include PTC material if desired.

For instance, in some other versions, electrodes (336, 338) do not comprise PTC material but a PTC material is used in sensor (340). In such versions, the resistance value of the PTC material forming sensor (340) may still change in response to the temperature of the tissue ($T_1$, $T_2$) increasing, and control module (256) may execute a control algorithm to reduce the RF energy delivered through electrodes (336, 338) in response to increases in the resistance value of the PTC material forming sensor (340). As another merely illustrative example, end effector (300) may include two discrete, spaced-apart sensors (340) that each comprise PTC material. In some such versions, control module (256) may monitor the resistance value of the PTC material from one sensor (340) to the other sensor (340) through the tissue that is being contacted by sensors (340). As yet another merely illustrative variation where two sensors (340) are used in this fashion, one sensor (340) may comprise a PTC material while the other sensor (340) may comprise a conductive non-PTC material that is unaffected by temperatures encountered during normal operation of end effector (300). Other suitable variations will be apparent to those of ordinary skill in the art in view of the teachings herein.

B. Exemplary End Effector with Clamp Arm Having Single Electrode

Figure 9:
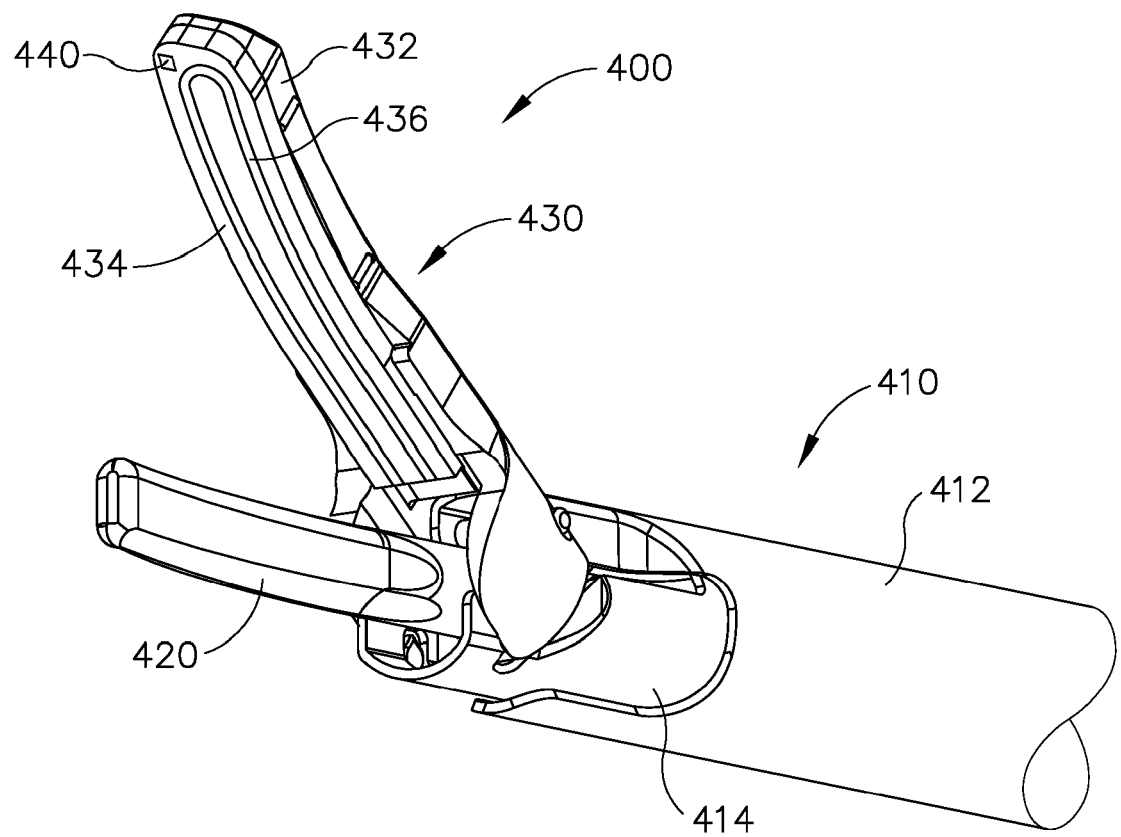
FIG. 9 depicts a perspective view of another exemplary alternative end effector that may be incorporated into the instrument of FIG. 2 to provide the arrangement of powered components of FIG. 6.
Figure 10:
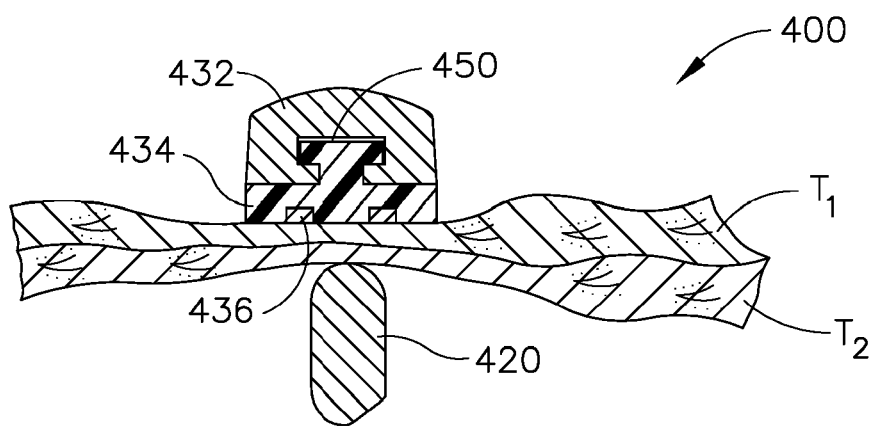
FIG. 10 depicts a cross-sectional end view of the end effector of FIG. 9 clamping tissue.

FIGS. 9-10 show another exemplary end effector (400) that may be incorporated into instrument (100) in place of end effector (140) in order to provide the functionality of system (250) described above. End effector (440) comprises a clamp arm (430) and an ultrasonic blade (420). End effector (440) is located at the distal end of a shaft assembly (410). Shaft assembly (410) includes an outer tube (412) and an inner tube (414). Clamp arm (430) is pivotably coupled with outer tube (412) and also with inner tube (414), such that clamp arm (430) is configured to pivot toward and away from blade (420) in response to relative movement between tubes (412, 414). Clamp arm (430) is thus pivotable just like clamp arm (144) described above. In some versions, outer tube (412) translates while inner tube (414) remains stationary in order to provide pivotal movement of clamp arm (430). In some other versions, inner tube (414) translates while outer tube (412) remains stationary in order to provide pivotal movement of clamp arm (430).

Blade (420) of the present example is configured and operable just like blade (24, 160) described above. Alternatively, blade (420) may have any other suitable configuration. It should be understood that, in the context of system (250) described above, blade (420) serves as part of acoustic drivetrain (258).

Clamp arm (430) of the present example is substantially similar to clamp arm (144) described above. In particular, clamp arm (430) comprises a clamp arm body (432) and a clamp pad (434) that is secured to clamp arm body (432) by a rail (450). By way of example only, clamp pad (434) may be formed of a polytetrafluoroethylene (PTFE) material and/or any other suitable material(s). Unlike clamp arm (144), clamp arm (430) of this example further includes an electrode (436) and a sensor (440). In the present example, electrode (436) is configured to provide one pole for application of bipolar RF electrosurgical energy while blade (420) provides another pole for application of bipolar RF electrosurgical energy to tissue that contacts electrode (436) and blade (420). It should be understood that, in the context of system described above, electrode (436) and blade (420) together serve as part of RF electrosurgical drivetrain (260).

In the present example, electrode (436) defines a "U" shape and extends along a substantial portion of the full length of clamp pad (434). In addition, electrode (436) is positioned inwardly from the outermost regions of clamp pad (434). In some alternative versions, electrode (436) extends along the outermost regions of clamp pad (434). As another merely illustrative example, electrode (436) may extend across the full width of clamp pad (434). Other suitable configurations and arrangements of electrode (436) will be apparent to those of ordinary skill in the art in view of the teachings herein.

Sensor (440) of the present example is located at the distal end of end effector (400) and is located just distal to electrode (436). This location is just one merely illustrative example. Other suitable locations for sensor (440) will be apparent to those of ordinary skill in the art in view of the teachings herein. It should also be understood that end effector (400) may include two or more sensors (440) if desired.

Sensor (440) of the present example is operable to sense a state of the tissue that is being engaged by clamp pad (434). In particular, sensor (440) is operable to sense one or more tissue conditions that would indicate that the tissue has reached the appropriate sealing temperature associated with line (204) as shown in FIG. 5 and as described above. By way of example only, sensor (440) may comprise a conventional temperature sensor. As another merely illustrative example, sensor (440) may comprise an impedance sensor (e.g., to the extent that the impedance of tissue is indicative of the tissue reaching an appropriate temperature or otherwise reaching a sealed state). As yet another merely illustrative example, sensor (440) may comprise a positive temperature coefficient (PTC) thermistor. Other suitable forms that sensor (440) may take will be apparent to those of ordinary skill in the art in view of the teachings herein. It should be understood that, in the context of system (250) described above, sensor (440) serves the purpose of sensor (262).

As shown in FIG. 10, end effector (400) may be used to clamp tissue ($T_1$, $T_2$) between clamp arm (430) and blade (420). While end effector (400) is shown as clamping two layers of tissue ($T_1$, $T_2$), it should be understood that some uses of end effector (400) may include clamping only one layer of tissue ($T_1$, $T_2$). In either case, end effector (400) may be activated to either just seal the tissue ($T_1$, $T_2$) or cut and seal the tissue ($T_1$, $T_2$). When end effector (400) is activated to apply RF electrosurgical energy, the RF electrosurgical energy may flow through the tissue ($T_1$, $T_2$) that is positioned between electrode (436) and blade (420). When end effector (400) is activated to apply ultrasonic energy, blade (420) applies the ultrasonic energy to the region of tissue clamped between clamp arm (430) and blade (420). As described in greater detail below, end effector (400) may apply RF electrosurgical energy and ultrasonic energy separately in a sequence; or together simultaneously. In either case, control module (256) may determine the appropriate algorithm for applying RF electrosurgical energy and/or ultrasonic energy.

While end effector (400) applies RF electrosurgical energy and/or ultrasonic energy to the tissue ($T_1$, $T_2$), sensor (440) may continuously detect one or more conditions associated with the tissue ($T_1$, $T_2$) and provide data to control module (256). Control module (256) may process this data as a factor of a control algorithm that is used to determine whether and how to apply RF electrosurgical energy and/or ultrasonic energy to the tissue ($T_1$, $T_2$). Various examples of control algorithms are described in greater detail below, while other examples of control algorithms will be apparent to those of ordinary skill in the art in view of the teachings herein.

In some versions, electrode (436) comprises PTC material. In some such versions, electrode (436) provides a resistance value that increases as the temperature of the tissue ($T_1$, $T_2$) increases. In some such versions, as the resistance of electrode (436) increases in response to the temperature of the tissue ($T_1$, $T_2$) increasing, the RF electrosurgical energy provided by electrode (436) diminishes, perhaps even ceasing once the temperature of the tissue ($T_1$, $T_2$) exceeds a threshold. Thus, in a sense the PTC material of electrode (436) may serve as a sensor (440) in addition to serving as an electrode, since the PTC material is sensitive to the condition of the tissue ($T_1$, $T_2$) and effectively changes the delivery of RF electrosurgical energy to the tissue ($T_1$, $T_2$) based on the condition of the tissue ($T_1$, $T_2$). Of course, electrode (436) need not necessarily include PTC material if desired.

For instance, in some other versions, electrode (436) does not comprise PTC material but a PTC material is used in sensor (440). In such versions, the resistance value of the PTC material forming sensor (440) may still change in response to the temperature of the tissue ($T_1$, $T_2$) increasing, and control module (256) may execute a control algorithm to reduce the RF energy delivered through electrode (436) and blade (420) in response to increases in the resistance value of the PTC material forming sensor (440). As another merely illustrative example, end effector (400) may include two discrete, spaced-apart sensors (440) that each comprise PTC material. In some such versions, control module (256) may monitor the resistance value of the PTC material from one sensor (440) to the other sensor (440) through the tissue that is being contacted by sensors (440). As yet another merely illustrative variation where two sensors (440) are used in this fashion, one sensor (440) may comprise a PTC material while the other sensor (440) may comprise a conductive non-PTC material that is unaffected by temperatures encountered during normal operation of end effector (400). Other suitable variations will be apparent to those of ordinary skill in the art in view of the teachings herein.

C. Exemplary Control Algorithms

The following examples include various control algorithms that may be executed through a control logic residing in control module (256) of system (250). It should also be understood that either of the end effectors (300, 400) described above may be used in the performance of these control algorithms. In addition or in the alternative, end effectors such as those described in U.S. Pat. No. 8,663,220 and/or U.S. Pub. No. 2015/0141981, issued as U.S. Pat. No. 9,949,785 on Apr. 24, 2018, may be used in the performance of these control algorithms. Other suitable end effectors that may be used in the performance of these control algorithms will be apparent to those of ordinary skill in the art in view of the teachings herein. It should be understood that each of the algorithms described below may begin as soon as an operator actuates a button (126) while clamping tissue ($T_1$, $T_2$) with end effector (300, 400).

Figure 11:
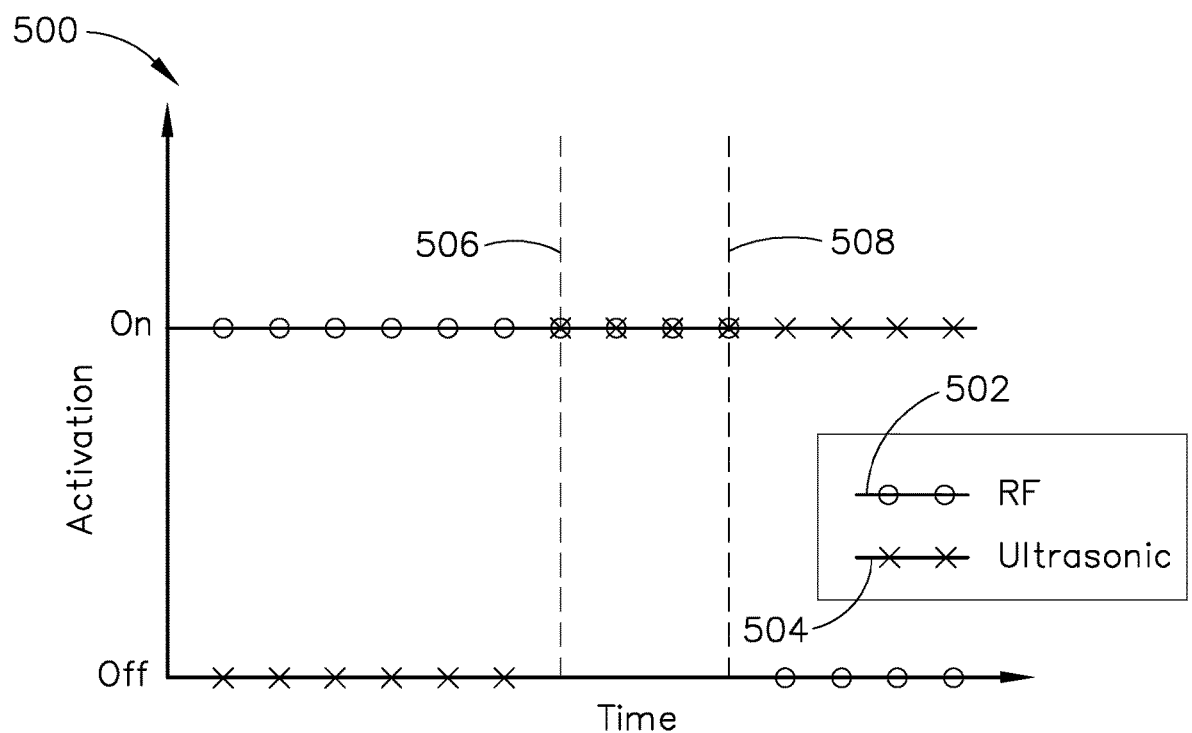
FIG. 11 depicts a graph showing an exemplary activation scheme that may be carried out using the arrangement of powered components of FIG. 6.
Figure 12:
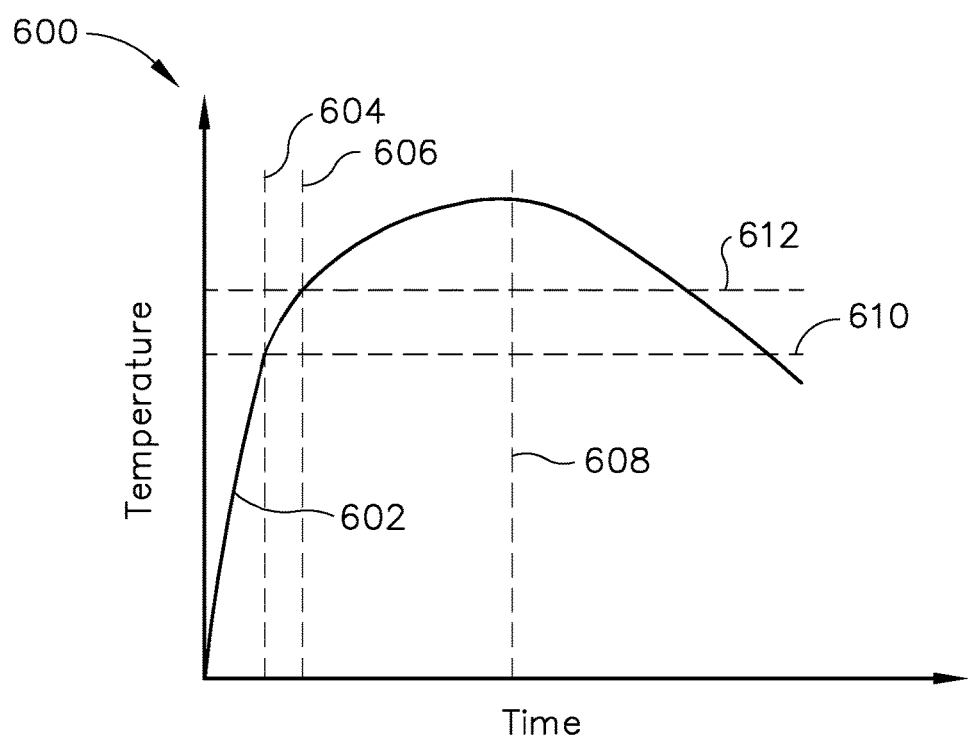
FIG. 12 depicts a graph showing a plot of tissue temperature versus time during execution of the activation scheme of FIG. 11.

FIG. 11 shows a graph (500) depicting an algorithm whereby an end effector (300, 400) may apply RF electrosurgical energy and ultrasonic energy to tissue ($T_1$, $T_2$) in a particular sequence and combination. FIG. 12 shows a graph (600) plotting tissue temperature (602) over the course of time while the tissue is clamped between clamp arm (330, 430) and blade (320, 420), during performance of the algorithm depicted in graph (500). In executing the algorithm of the present example, control module (256) first activates end effector (300, 400) to apply RF electrosurgical energy to the tissue. In graph (500), the RF electrosurgical energy is represented by the line (502) with spaced apart circles. As shown in FIG. 12, this RF electrosurgical energy provides a rapid increase in the tissue temperature (602), resulting in the tissue ($T_1$, $T_2$) beginning to seal relatively quickly after the control algorithm is first executed. Line (612) represents the temperature level at which the tissue ($T_1$, $T_2$) will begin to seal. Similarly, line (606) represents the time at which the tissue ($T_1$, $T_2$) begins to seal. It should be understood from a comparison between the graph (200) of FIG. 5 and the graph (600) of FIG. 12 that the tissue ($T_1$, $T_2$) will begin to seal much more quickly when RF electrosurgical energy is used at the beginning of the process.

In the present example, the control algorithm includes a period of overlap where control module (256) activates end effector (300, 400) to apply RF electrosurgical energy and ultrasonic energy simultaneously. In the graph (500) of FIG. 11, this occurs at the moment in time represented by line (506). In graph (500), the ultrasonic energy is represented by the line (504) with spaced apart x's. In the graph (600) of FIG. 12, this occurs at the moment in time represented by line (604). It should therefore be understood that lines (506, 604) represent the same moment in time. This moment in time is associated with the tissue ($T_1$, $T_2$) reaching a temperature level (610) that is just below the temperature level (612) where sealing actually begins. Once the sealing actually begins, control module (256) ceases application of RF electrosurgical energy via end effector (300, 400), such that end effector (300, 400) only applies ultrasonic energy. This transition occurs at the moment in time represented by line (508) in graph (500) of FIG. 11. It should therefore be understood that lines (508, 606) represent the same moment in time.

During the power mode overlap period between the moment represented by lines (506, 604) and the moment represented by lines (508, 606), the power level of the RF electrosurgical energy may be gradually decreased to zero. Alternatively, the power level of the RF electrosurgical energy may be constant during the power mode overlap period between the moment represented by lines (506, 604) and the moment represented by lines (508, 606). Regardless of whether the power level of the RF electrosurgical energy remains constant or changes during the power mode overlap period between the moment represented by lines (506, 604) and the moment represented by lines (508, 606), the power level of the ultrasonic energy may gradually increase or may be immediately activated at the predetermined power level. When control module (256) ceases application of RF electrosurgical energy via end effector (300, 400), the temperature of the tissue ($T_1$, $T_2$) may continue to increase, at a rate that will depend on the amount of ultrasonic energy being imparted to the tissue ($T_1$, $T_2$) via end effector (300, 400).

It should be understood that the tissue ($T_1$, $T_2$) will be actively sealed during the time period between the moments represented by lines (606, 608). As shown in FIG. 12, the tissue temperature (602) continues to increase during the duration represented by the space between lines (606, 608). However, the rate of increase during this duration is less than the rate of increase encountered during the pre-heating stage, which occurs before and up to the moment represented by line (604). In other words, the tissue heating is more gradual during the duration represented by the space between lines (606, 608) than the tissue heating encountered before and up to the moment represented by line (604). In some other versions, the tissue temperature (602) remains substantially constant, at the level (612) associated with sealing, during the time period represented by the space between lines (606, 608). In some such versions, control module (256) may regulate the delivery of ultrasonic power through blade (320, 420) in order to provide substantial constancy in the tissue temperature (602) during this period. In some such versions, control module (256) relies on feedback from sensor (340, 440) in order to regulate the delivery of ultrasonic power through blade (320, 420) in order to provide substantial constancy in the tissue temperature (602).

Once the tissue ($T_1$, $T_2$) has been appropriately sealed, control module (256) may deactivate the ultrasonic power, which may result in a decrease in the tissue temperature (602). The moment in time in which the ultrasonic power is deactivated is represented by line (608) in FIG. 12. In some versions, this deactivation of ultrasonic power is automatically provided by control module (256). By way of example only, control module (256) may automatically deactivate ultrasonic power in response to data from sensor (340, 440). In addition or in the alternative, control module (256) may automatically deactivate ultrasonic power in response to data from a timer and/or some other component. As yet another merely illustrative alternative, ultrasonic power may be manually deactivated by the operator, such as by releasing an activation button (126).

It should also be understood that control module (256) may automatically provide the power mode transitions at the moments represented by lines (506, 508) in response to data from sensor (340, 440). For instance, when sensor (340, 440) detects that the tissue temperature (602) has surpassed the first threshold level (610), control module (256) may respond by automatically activating ultrasonic energy while maintaining the activation of RF electrosurgical energy. When sensor (340, 440) detects that tissue temperature (602) has reached the level (612) associated with tissue sealing, control module (256) may respond by automatically deactivating RF electrosurgical energy while maintaining the activation of ultrasonic energy. In versions where electrodes (336, 338, 436) comprise PTC material, the change in resistance that is provided by the PTC material may effect the deactivation of RF electrosurgical energy through end effector (300, 400). In such versions, control module (256) need not provide any kind of switching to deactivate the RF electrosurgical energy.

In addition to or in lieu of being based on data from sensor (340, 440), the power mode transitions provided by control module (256) may be based on the passage of time. For instance, control module (256) may execute a control algorithm that provides only RF energy to tissue via end effector (300, 400) for a certain predetermined duration, followed by a combination of RF energy and ultrasonic energy to tissue via end effector (300, 400) for a subsequent predetermined duration, followed by only ultrasonic energy to tissue via end effector (300, 400). As another merely illustrative example, control module (256) may execute a control algorithm that provides only RF energy to tissue via end effector (300, 400) for a certain predetermined duration, followed by only ultrasonic energy to tissue via end effector (300, 400). It should therefore be understood that sensor (340, 440) may be omitted in some versions. As yet another merely illustrative variation, control module (256) may rely on a combination of data from sensor (340, 440) and data from a timer to combine tissue conditions and time conditions as factors in execution of a control algorithm to provide power mode transitions through end effector (300, 400).

The above described power mode transitions may occur while the operator continues to actuate button (126), such that the operator does not need to perform in any separate acts in order to provide these power mode transitions. In some versions, control module (256) may trigger one or more forms of audible feedback and/or visual feedback to indicate to the operator that end effector (300, 400) is providing power mode transitions. Various suitable ways in which the operator may receive this feedback will be apparent to those of ordinary skill in the art in view of the teachings herein.

Figure 13:
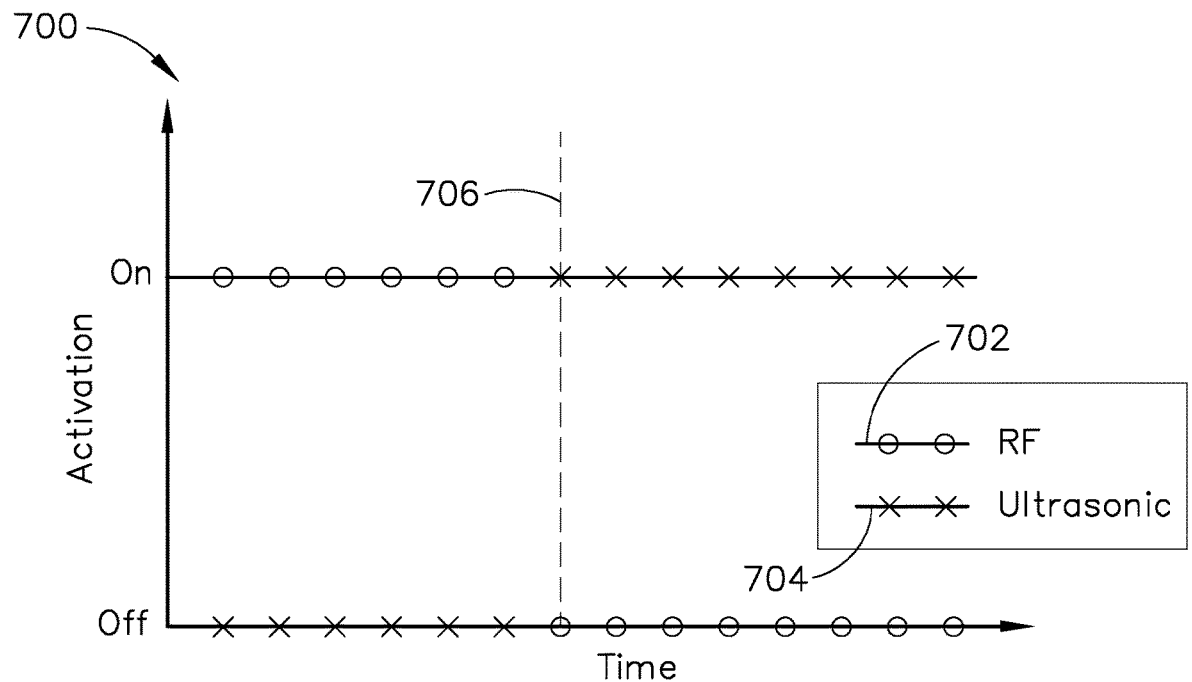
FIG. 13 depicts a graph showing an exemplary alternative activation scheme that may be carried out using the arrangement of powered components of FIG. 6.

FIG. 13 shows a graph (700) depicting another algorithm whereby an end effector (300, 400) may apply RF electrosurgical energy and ultrasonic energy to tissue ($T_1$, $T_2$) in a particular sequence and combination. In executing the algorithm of the present example, control module (256) first activates end effector (300, 400) to apply RF electrosurgical energy to the tissue. In graph (700), the RF electrosurgical energy is represented by the line (702) with spaced apart circles. As noted above and as shown in FIG. 12, this RF electrosurgical energy provides a rapid increase in the tissue temperature (602), resulting in the tissue ($T_1$, $T_2$) beginning to seal relatively quickly after the control algorithm is first executed. So again, the tissue ($T_1$, $T_2$) will begin to seal much more quickly when RF electrosurgical energy is used at the beginning of the process as compared to just ultrasonic energy.

Unlike the algorithm shown in graph (500) of FIG. 11, the algorithm shown in graph (700) provides a toggle from RF electrosurgical energy to ultrasonic energy, such that there is no period of overlap where RF electrosurgical energy and ultrasonic energy are applied simultaneously. In graph (700), the ultrasonic energy is represented by the line (704) with spaced apart x's. The moment at which this power mode transition occurs is represented by line (706) in graph (700) of FIG. 13. In some versions, this moment represented by line (706) in graph (700) of FIG. 13 may coincide with the moment represented by line (604) in graph (600) of FIG. 12. In other words, control module (256) may toggle from only RF electrosurgical energy to only ultrasonic energy once the tissue temperature (602) passes a first threshold level (610) that is just below the level (612) where tissue sealing actually begins. In some other versions, the moment represented by line (706) in graph (700) of FIG. 13 may coincide with the moment represented by line (606) in graph (600) of FIG. 12. In other words, control module (256) may toggle from only RF electrosurgical energy to only ultrasonic energy once the tissue temperature (602) reaches the level (612) where tissue sealing actually begins.

Figure 14:
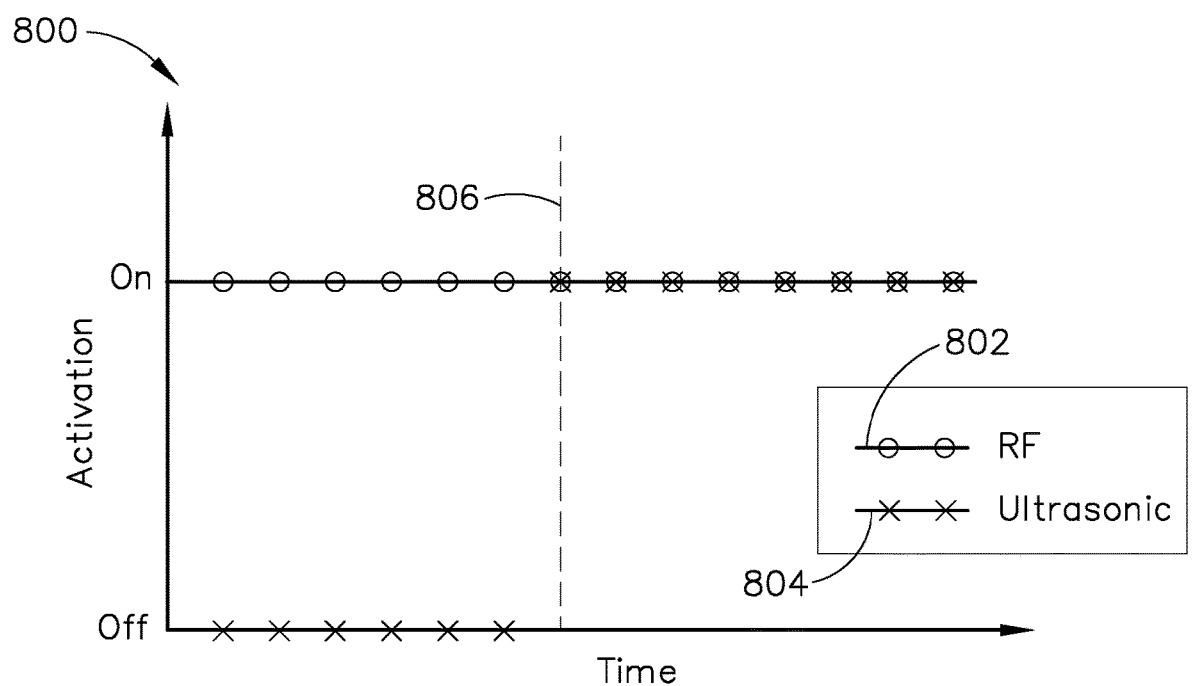
FIG. 14 depicts a graph showing another exemplary alternative activation scheme that may be carried out using the arrangement of powered components of FIG. 6.

FIG. 14 shows a graph (800) depicting another algorithm whereby an end effector (300, 400) may apply RF electrosurgical energy and ultrasonic energy to tissue ($T_1$, $T_2$) in a particular sequence and combination. In executing the algorithm of the present example, control module (256) first activates end effector (300, 400) to apply RF electrosurgical energy to the tissue. In graph (800), the RF electrosurgical energy is represented by the line (802) with spaced apart circles. As noted above and as shown in FIG. 12, this RF electrosurgical energy provides a rapid increase in the tissue temperature (602), resulting in the tissue ($T_1$, $T_2$) beginning to seal relatively quickly after the control algorithm is first executed. So again, the tissue ($T_1$, $T_2$) will begin to seal much more quickly when RF electrosurgical energy is used at the beginning of the process as compared to just ultrasonic energy.

Unlike the algorithm shown in graph (500) of FIG. 11, the algorithm shown in graph (800) provides a sustained combination of RF electrosurgical energy and ultrasonic energy. In graph (800), the ultrasonic energy is represented by the line (804) with spaced apart x's. The moment at which this power mode transition occurs is represented by line (806) in graph (800) of FIG. 14. In some versions, this moment represented by line (806) in graph (800) of FIG. 14 may coincide with the moment represented by line (604) in graph (600) of FIG. 12. In other words, control module (256) may toggle from only RF electrosurgical energy to a combination of RF electrosurgical energy and ultrasonic energy once the tissue temperature (602) passes a first threshold level (610) that is just below the level (612) where tissue sealing actually begins. In some other versions, the moment represented by line (806) in graph (800) of FIG. 14 may coincide with the moment represented by line (606) in graph (600) of FIG. 12. In other words, control module (256) may toggle from only RF electrosurgical energy to a combination of RF electrosurgical energy and ultrasonic energy once the tissue temperature (602) reaches the level (612) where tissue sealing actually begins.

As noted above, the tissue ($T_1$, $T_2$) will be actively sealed during the time period between the moments represented by lines (606, 608). As also noted above and as shown in FIG. 12, the tissue temperature (602) remains substantially constant, at the level (612) associated with sealing, during this time period. In some versions, control module (256) may regulate the combined delivery of RF electrosurgical energy and ultrasonic power through end effector (300, 400) in order to provide constancy in the tissue temperature (602) during this period. In some such versions, control module (256) relies on feedback from sensor (340, 440) in order to regulate the combined delivery of RF electrosurgical energy and ultrasonic power through end effector (300, 400) in order to provide constancy in the tissue temperature (602). By way of example only, control module (256) may raise or lower the power level of the RF electrosurgical energy and/or raise or lower the ultrasonic power level during the time period between the moments represented by lines (606, 608), based ion data from sensor (340, 440), in order to provide constancy in the tissue temperature (602). As another merely illustrative example, control module (256) may determine whether RF electrosurgical energy or ultrasonic energy is the most appropriate power mode for a particular moment during the time period between the moments represented by lines (606, 608), and switch between these power modes accordingly, based on data from sensor (340, 440).

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly, wherein the shaft assembly extends distally from the body, wherein the shaft assembly comprises an acoustic waveguide, wherein the waveguide is configured to acoustically couple with an ultrasonic transducer; (c) an end effector, wherein the end effector comprises: (i) an ultrasonic blade in acoustic communication with the waveguide, (ii) a clamp arm, wherein the clamp arm is operable to compress tissue against the ultrasonic blade, (iii) an electrode, wherein the electrode is operable to apply radiofrequency (RF) electrosurgical energy to tissue, and (iv) a sensor, wherein the sensor is operable to sense a condition of tissue contacted by the end effector; and (d) a control module, wherein the control module is operable to control delivery of ultrasonic power and RF electrosurgical energy through the end effector based on data from the sensor.

Example 2

The apparatus of Example 1, wherein the control module is configured to: (i) first, activate the end effector to apply only RF electrosurgical energy to tissue captured between the clamp arm and the ultrasonic blade, and (ii) second, activate the end effector to apply ultrasonic energy to tissue captured between the clamp arm and the ultrasonic blade after the RF electrosurgical energy has been applied.

Example 3

The apparatus of Example 2, wherein the control module is configured to automatically transition from activating the end effector to apply only RF electrosurgical energy to tissue to activating the end effector to apply ultrasonic energy to tissue based on data from the sensor.

Example 4

The apparatus of Example 3, wherein the control module is configured to automatically transition from activating the end effector to apply only RF electrosurgical energy to tissue to activating the end effector to apply ultrasonic energy to tissue based on data from the sensor indicating that the tissue has reached a certain temperature.

Example 5

The apparatus of any one or more of Examples 2 through 4, wherein the control module is configured to automatically cease activation of the end effector to apply only RF electrosurgical energy to tissue when the control module activates the end effector to apply ultrasonic energy to tissue, such that the end effector only applies ultrasonic energy to tissue after only applying RF electrosurgical energy to tissue.

Example 6

The apparatus of Example 1, wherein the control module is configured to: (i) first, activate the end effector to apply only RF electrosurgical energy to tissue captured between the clamp arm and the ultrasonic blade, and (ii) second, activate the end effector to apply a combination of RF electrosurgical energy and ultrasonic energy to tissue captured between the clamp arm and the ultrasonic blade after the RF electrosurgical energy has been applied.

Example 7

The apparatus of Example 6, wherein the control module is configured to automatically transition from activating the end effector to apply only RF electrosurgical energy to tissue to activating the end effector to apply a combination of RF electrosurgical energy and ultrasonic energy to tissue based on data from the sensor.

Example 8

The apparatus of any one or more of Examples 6 through 7, wherein the control module is further configured to, third, apply only ultrasonic energy to tissue captured between the clamp arm and the ultrasonic blade after the combination of RF electrosurgical energy and ultrasonic energy has been applied.

Example 9

The apparatus of Example 8, wherein the control module is further configured to modulate between applying ultrasonic energy and RF electrosurgical energy in order to provide a substantially constant tissue temperature.

Example 10

The apparatus of any one or more of Examples 1 through 9, wherein the electrode is integrated into the clamp arm.

Example 11

The apparatus of any one or more of Examples 1 through 10, wherein the electrode and the ultrasonic blade are configured to cooperate to apply bipolar RF electrosurgical energy to tissue.

Example 12

The apparatus of any one or more of Examples 1 through 11, wherein the sensor is integrated into the clamp arm.

Example 13

The apparatus of any one or more of Examples 1 through 12, wherein the sensor comprises a temperature sensor.

Example 14

The apparatus of any one or more of Examples 1 through 13, wherein the sensor comprises an impedance sensor.

Example 15

The apparatus of any one or more of Examples 1 through 14, wherein the sensor comprises a positive temperature coefficient (PTC) thermistor.

Example 16

An apparatus comprising: (a) a body; (b) a shaft assembly, wherein the shaft assembly extends distally from the body, wherein the shaft assembly comprises an acoustic waveguide, wherein the waveguide is configured to acoustically couple with an ultrasonic transducer; (c) an end effector, wherein the end effector comprises: (i) an ultrasonic blade in acoustic communication with the waveguide, and (ii) a clamp arm, wherein the clamp arm is operable to compress tissue against the ultrasonic blade, wherein the clamp arm and the ultrasonic blade are operable to cooperate to apply bipolar radiofrequency (RF) electrosurgical energy to tissue; (d) a sensor, wherein the sensor is operable to sense a condition of tissue contacted by the end effector; and (e) a control module, wherein the control module is operable to: (i) activate the end effector to pre-heat tissue with RF electrosurgical energy in a pre-heating stage, (ii) activate the end effector to seal tissue with ultrasonic energy in a sealing stage, and (iii) automatically transition from the pre-heating stage to the sealing stage based on data from the sensor.

Example 17

A method of sealing tissue, comprising: (a) applying radiofrequency (RF) electrosurgical energy to tissue to thereby pre-heat the tissue; (b) sensing a condition associated with the temperature of the tissue while performing the act of applying RF electrosurgical energy to the tissue; (c) detecting a condition indicating that the temperature of the tissue has reached a predetermined level; and (d) applying ultrasonic energy to the tissue to seal the tissue, wherein the act of applying ultrasonic energy to the tissue is initiated based on the act of detecting the condition indicating that the temperature of the tissue has reached the predetermined level.

Example 18

The method of Example 17, further comprising ceasing the act of applying radiofrequency (RF) electrosurgical energy to tissue in response to the act of detecting the condition indicating that the temperature of the tissue has reached the predetermined level.

Example 19

The method of Example 17, wherein the act of applying radiofrequency (RF) electrosurgical energy continues to be performed during performance of the act of applying ultrasonic energy to the tissue to seal the tissue.

Example 20

The method of Example 17, wherein the act of applying radiofrequency (RF) electrosurgical energy continues to be performed for a first period during performance of the act of applying ultrasonic energy to the tissue to seal the tissue, wherein the act of applying radiofrequency (RF) electrosurgical energy ceases during a second period during performance of the act of applying ultrasonic energy to the tissue to seal the tissue.

Example 21

A method of sealing tissue, comprising: (a) applying radiofrequency (RF) electrosurgical energy to tissue via an end effector to thereby pre-heat the tissue; and (b) automatically applying ultrasonic energy to the pre-heated tissue via the end effector to thereby seal the pre-heated tissue, wherein the act of automatically applying ultrasonic energy to the pre-heated tissue via the end effector is initiated upon passage of a predetermined period of time after the act of applying RF electrosurgical energy is initiated.

Example 22

The method of Example 21, further comprising ceasing the act of applying RF electrosurgical energy to the tissue upon passage of the predetermined period of time.

V. MISCELLANEOUS

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An ultrasonic surgical instrument, comprising:
   (a) an end effector, including:
      (i) an ultrasonic blade configured to connect to an acoustic waveguide for acoustic communication of an ultrasonic energy to the ultrasonic blade for applying to a tissue,
      (ii) a first electrode configured to receive a radiofrequency (RF) electrosurgical energy for applying to the tissue, and
      (iii) a sensor configured to sense a first condition of the tissue; and
   (b) a control module operatively connected to the ultrasonic blade, the first electrode and the sensor, wherein the control module has a control logic with a first predetermined tissue condition level residing thereon, wherein the control logic is configured to receive the first condition of the tissue from the sensor and determine when the first condition has reached the first predetermined condition level such that the control module adjusts activation of at least one of the ultrasonic or RF electrosurgical energies from the ultrasonic blade or first electrode, respectively, in response to the first condition reaching the first predetermined condition level,
   wherein the control module is configured to activate the end effector to apply only RF electrosurgical energy prior to the control module determining that the tissue has reached the first predetermined condition level for pre-heating the tissue with the RF electrosurgical energy.

2. The ultrasonic surgical instrument of claim 1, wherein the first electrode is incorporated into the ultrasonic blade.

3. The ultrasonic surgical instrument of claim 1, wherein the end effector further includes a clamp arm movably mounted relative to the ultrasonic blade and configured to compress the tissue against the ultrasonic blade.

4. The ultrasonic surgical instrument of claim 3, wherein the first electrode is secured to the clamp arm.

5. The ultrasonic surgical instrument of claim 4, wherein the end effector further includes a second electrode, and wherein the second electrode is secured to the clamp arm.

6. The ultrasonic surgical instrument of claim 3, wherein the sensor is secured to the clamp arm.

7. The ultrasonic surgical instrument of claim 1, wherein the sensor is incorporated into the ultrasonic blade.

8. The ultrasonic surgical instrument of claim 1, wherein the sensor is incorporated into the first electrode.

9. The ultrasonic surgical instrument of claim 1, wherein the sensor includes a temperature sensor.

10. The ultrasonic surgical instrument of claim 1, wherein the sensor includes an impedance sensor.

11. The ultrasonic surgical instrument of claim 1, wherein the sensor includes a positive temperature coefficient thermistor.

12. The ultrasonic surgical instrument of claim 1, wherein the sensor includes an optical sensor.

13. The ultrasonic surgical instrument of claim 1, wherein the first condition of the tissue is a first temperature of the tissue, wherein the first predetermined tissue condition level is a first predetermined tissue temperature level, and wherein the control module is configured to activate the end effector to apply only RF electrosurgical energy prior to the control module determining that the tissue has reached the first temperature for pre-heating the tissue with the RF electrosurgical energy.

14. The ultrasonic surgical instrument of claim 13, wherein the control module is further configured to adjust the activation of at least one of the ultrasonic or electrosurgical energies from the ultrasonic blade or first electrode, respectively, in response to the first temperature of the tissue reaching the first predetermined tissue temperature level such that the control module activates at least the ultrasonic energy.

15. The ultrasonic surgical instrument of claim 14, wherein the control module is further configured to regulate activation at least one of the ultrasonic or RF electrosurgical energies from the ultrasonic blade or first electrode in response to the first temperature of the tissue reaching the first predetermined tissue temperature level to thereby provide consistency of the first temperature of the tissue at the first predetermined tissue temperature level.

16. An ultrasonic surgical instrument, comprising:
   (a) an end effector, including:
      (i) an ultrasonic blade configured to connect to an acoustic waveguide for acoustic communication of an ultrasonic energy to the ultrasonic blade for applying to a tissue,
      (ii) a first electrode configured to receive a radiofrequency (RF) electrosurgical energy for applying to the tissue,
      (iii) a sensor configured to sense a first condition of the tissue; and
   (b) a control module operatively connected to the ultrasonic blade, the first electrode and the sensor, wherein the control module has a control logic with a first predetermined tissue temperature level residing thereon, wherein the control logic is configured to receive the first condition of the tissue from the sensor and determine a first temperature of the tissue based on the first condition, and wherein the control logic is further configured to determine that the first temperature of the tissue is below the first predetermined tissue temperature level such that the control module activates the end effector with only RF electrosurgical energy for pre-heating the tissue.

17. The ultrasonic surgical instrument of claim 16, wherein the control module is further configured to determine when the first temperature has reached the first predetermined temperature level such that the control module activates at least the ultrasonic energy in response to the first temperature of the tissue reaching the first predetermined temperature level.

18. The ultrasonic surgical instrument of claim 16, wherein the first electrode is incorporated into the ultrasonic blade.

19. The ultrasonic surgical instrument of claim 16, wherein the sensor is incorporated into the ultrasonic blade.

20. A method of pre-heating a tissue with an ultrasonic surgical instrument, the ultrasonic surgical instrument including: (a) an end effector, including: (i) an ultrasonic blade configured to connect to an acoustic waveguide for acoustic communication of an ultrasonic energy to the ultrasonic blade for applying to a tissue, (ii) a first electrode configured to receive a radiofrequency (RF) electrosurgical energy for applying to the tissue, and (iii) a sensor configured to sense a first condition of the tissue; and (b) a control module operatively connected to the ultrasonic blade, the first electrode and the sensor, wherein the control module has a control logic with a first predetermined tissue condition level residing thereon, wherein the control logic is configured to receive the first condition of the tissue from the sensor and determine when the first condition has reached the first predetermined condition level such that the control module adjusts activation of at least one of the ultrasonic or RF electrosurgical energies from the ultrasonic blade or first electrode, respectively, in response to the first condition reaching the first predetermined condition level, the method comprising:
  (a) activating the end effector with only RF electrosurgical energy to apply thereby pre-heating the tissue;
  (b) determining that the first condition has reached the first predetermined condition level after pre-heating the tissue; and
  (c) adjusting activation of at least one of the ultrasonic or RF electrosurgical energies from the ultrasonic blade or first electrode, respectively, in response to the first condition reaching the first predetermined condition level after pre-heating the tissue.

* * * * *